United States Patent [19]
Cohen et al.

[11] Patent Number: 5,610,199
[45] Date of Patent: Mar. 11, 1997

[54] SOLID LIPOPHILIC COMPOSITION AND PROCESS FOR ITS PREPARATION

[75] Inventors: Isaac D. Cohen, Brooklyn; Andrew J. Bevacqua, East Setauket; Daniela Toma, Floral Park; Konstantinos M. Lahanas, No. Babylon, all of N.Y.

[73] Assignee: Estee Lauder Inc., New York, N.Y.

[21] Appl. No.: 365,810

[22] Filed: Dec. 29, 1994

Related U.S. Application Data

[63] Continuation-in-part of Ser. No. 216,151, Mar. 22, 1994, abandoned.

[51] Int. Cl.$^6$ .......................... A61K 31/075; A61K 7/42
[52] U.S. Cl. ..................... 514/721; 424/59; 424/60; 424/400; 424/401; 512/20; 514/937; 514/938; 514/939
[58] Field of Search .................. 424/59, 60; 512/4, 512/20; 514/721

[56] References Cited

U.S. PATENT DOCUMENTS

| | | | |
|---|---|---|---|
| 3,630,896 | 12/1971 | Oka et al. | 252/1 |
| 4,154,816 | 5/1979 | Roehl et al. | 424/68 |
| 4,346,079 | 8/1982 | Roehl | 424/65 |
| 4,518,582 | 5/1985 | Schamper et al. | 424/66 |
| 4,719,102 | 1/1988 | Randhawa et al. | 424/66 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,839,161 | 6/1989 | Bowser et al. | 424/59 |
| 4,944,937 | 7/1990 | McCall | 424/65 |
| 5,039,513 | 8/1991 | Chatterjee et al. | 424/47 |
| 5,091,171 | 2/1992 | Yu et al. | 424/642 |
| 5,286,755 | 2/1994 | Kauffmann et al. | 514/944 |

FOREIGN PATENT DOCUMENTS

| | | |
|---|---|---|
| 0175074 | 3/1986 | European Pat. Off. . |
| 0260030 | 3/1988 | European Pat. Off. . |
| 0447318 | 9/1991 | European Pat. Off. . |
| WO91/15191 | 10/1991 | European Pat. Off. . |
| 0451002 | 10/1991 | European Pat. Off. . |
| 0504203 | 10/1992 | European Pat. Off. . |
| 57-84529 | 11/1983 | Japan . |
| 58-101205 | 12/1983 | Japan . |
| 60-075405 | 8/1985 | Japan . |

OTHER PUBLICATIONS

CFTA International Cosmetic Ingredient Dictionary, 4th Ed., pp. 56, 209, 210, 367, 459, 460, 502, 527 (J. M. Nikitakis, et al. ets. Cosmetic, Toiletry and Fragrance Association, Inc. Washington, 1991).

Primary Examiner—Shelley A. Dodson
Attorney, Agent, or Firm—Fish & Neave; Richard M. Barnes

[57] ABSTRACT

The present invention relates to solid lipophilic compositions suitable for topical application to human skin and to methods for preparing and using such compositions. The solid lipophilic compositions of the invention comprise dibenzyl monosorbitol acetal (DBMSA), lipophilic materials and one or more cosmetic materials.

21 Claims, No Drawings

SOLID LIPOPHILIC COMPOSITION AND PROCESS FOR ITS PREPARATION

CROSS REFERENCE TO RELATED APPLICATION

This application is a continuation-in-part of applicants' co-pending U.S. patent application Ser. No. 08/216,151, filed Mar. 22, 1994, now abandoned.

TECHNICAL FIELD OF THE INVENTION

The present invention relates to solid, lipophilic compositions suitable for topical application to human skin. In particular the invention relates to solid lipophilic compositions comprising dibenzyl monosorbitol acetal (DBMSA), lipophilic materials and one or more cosmetic materials.

The invention further relates to methods for preparing and using the compositions.

BACKGROUND OF THE INVENTION

Dibenzyl monosorbitol acetal, herein referred to as DBMSA is a known gelling agent. For example, DBMSA has been used as a gelling agent in transparent or translucent deodorant and antiperspirant sticks. See, for example, U.S. Pat. Nos. 4,154,816, 4,346,079, 4,518,582, 4,725,430, 4,743,444, 4,816,261, and 4,781,917 and European patent applications 260,030 and 451,002. Hydrophilic solvents, such as lower monohydric alcohols, are typically used in such deodorant and antiperspirant sticks to solubilize the DBMSA at elevated temperatures.

The use of hydrophilic solvents to solubilize DBMSA in many compositions containing cosmetic colorants, fragrances, sunscreens or dermatologic agents poses a number of problems. Such solvents are generally irritating and are undesirable in compositions for use on areas having mucus membranes (e.g., the areas around the lips or eyes.) Furthermore, hydrophilic solvents are generally incompatible with lipophilic colorants that are frequently found in cosmetic preparations. In addition, lower monohydric alcohols, such as ethanol, are incompatible with certain sun care and antiinflammatory agents because they adversely effect the skin protective qualities of these agents.

Stable cosmetic and dermatologic compositions have been prepared by melting together one or more lipophilic waxes and the appropriate cosmetic or dermatologic agents. The lipophilic wax-containing compositions are then transferred to suitable containers for cooling and solidification. Frequently, however, the resulting compositions containing high levels of lipophilic waxes are perceived to be excessively sticky or greasy upon application.

An object of the present invention is to provide stable, solid lipophilic compositions containing DBMSA, a lipophilic material and a cosmetic material which are suitable for topical application to human skin. It is a further object of this invention to provide stable, solid lipophilic compositions containing DBMSA, a lipophilic material and a cosmetic material that are not perceived as being sticky or greasy. A further object of this invention is to provide stable, lipophilic compositions containing DBMSA and hydroxyacid derivatives. An additional object of this invention is to provide methods for preparing such compositions. Yet a further object of this invention is to provide methods for applying color to human skin, for protecting human skin from sunlight, and for treating dermatologic disorders such as dry skin, wrinkles, and blemished skin, using the lipophilic DBMSA based compositions of this invention.

SUMMARY OF THE INVENTION

The compositions of the present invention comprise:
(a) from about 1.5% by weight to about 30% by weight of DBMSA;
(b) from about 70% by weight to about 98.0% by weight of lipophilic material; and
(c) from about 0.5% to about 28.5% by weight of a cosmetic material selected from the group consisting of colorants, fragrances, sunscreens, dermatologic agents, and mixtures thereof.

The present invention also relates to methods for preparing such compositions, which comprise the steps of:
(a) mixing DBMSA with one or more lipophilic materials at a temperature and for a period of time (e.g., about 15 min to about 45 min) sufficient to dissolve the DBMSA in the lipophilic material;
(b) mixing a cosmetic material selected from the group consisting of colorants, fragrances, sunscreens, dermatologic agents and mixtures therefore with the admixture of DBMSA and one or more lipophilic materials, the amounts of the materials being adjusted such that the resulting mixture contains from about 1.5% by weight to about 30% by weight DBMSA, from about 70% by weight to about 98.0% by weight of lipophilic material, and from about 0.5% by weight to about 28.5% by weight of cosmetic material; and
(c) cooling the mixture to ambient temperature.

It is to be understood that step (b) set forth above may be conducted prior to the DBMSA being dissolved in the lipophilic material, or during or after the dissolution step. In other words, the cosmetic material may be mixed with the other components of the mixture before or after the DBMSA is dissolved in the lipophilic material or while the dissolution step is being conducted. It will be understood further that the terms "mixture" and "mixing" in this application are used in the broad sense of the words with term "mixture" including, without limitation, blends, solutions, and suspensions.

The compositions of this invention are chemically and physically stable, nonirritating, and aesthetically pleasing. The compositions of this invention may comprise hydroxyacid derivatives which decompose in an aqueous environment to release products that are beneficial to the skin. In addition, the compositions of the invention may be made to be substantially non-greasy and non-sticky by utilizing lipophilic oils as the only or primary lipophilic material in the composition. Preferably, at least 80% by weight of the lipophilic material is a lipophilic oil (as opposed to a lipophilic wax) to achieve a composition that is substantially non-greasy and non-sticky.

DETAILED DESCRIPTION OF THE INVENTION

The compositions described herein comprise from about 1.5% by weight to about 30% by weight DBMSA. Preferably the compositions comprise about 2.0% by weight to about 5.0% by weight DBMSA. DBMSA suitable for use in the invention may be obtained from a number of commercial sources. Among the commercially available sources of DBMSA are MILLITHIX™ 925 (obtained from Milliken Chemical, a division of Milliken & Company, Spartansburg, S.C.), GELL-All-D™ (obtained from New Japan Chemical Company, Ltd.), and DISORBENE™ obtained from ROQUETTE Freres, France.)

The concentration of DBMSA in a particular composition influences the hardness and clarity of the composition, as well as the level of product transfer to the skin upon application. Appropriate concentrations can be readily determined by one of skill in the art, and will vary depending on the solubility of the DBMSA in the composition. In general, an increase in the concentration of DBMSA will provide a harder, less transparent composition, and a lower level of product transfer to the skin upon application. Conversely, a decrease in the concentration of DBMSA will provide a softer, more transparent composition, and a higher level of product transfer to the skin upon application.

The compositions of this invention also comprise from about 70% by weight to about 98.0% by weight of a lipophilic material. Lipophilic material, as used herein, refers to a non-polar material that is miscible in lipids. One class of lipophilic materials that may be used in the invention is lipophilic material from the class of materials known as cosmetically acceptable esters, e.g., mono-, di- and tri-esters having an alcohol chain length of 1 to 22 and an acid chain length of 1 to 22. Persons skilled in the art recognize that the group of cosmetically acceptable esters is very large, and can be further subdivided into, e.g., oils, waxes, glyceryl esters aliphatic esters and fats. See, e.g., CFTA *International Cosmetic Ingredient Dictionary*, 4th ed. (J. M. Nikitakis, et al. eds. Cosmetic, Toiletry and Fragrance Association, Inc. Washington, 1991).

Preferably at least about 80% by weight, most preferably at least about 95% by weight of the lipophilic material is one or more lipophilic oils. As used herein, the term lipophilic oils, refers to lipophilic materials that are liquid at room temperature about 17° C. to about 25° C. Preferred lipophilic oils for use in the invention are selected from the group consisting of castor oil, mineral oil, squalene, fatty acids (e.g., oleic acid), fatty alcohols (e.g., octyldodecanol), $C_{12-15}$ alkyl benzoate, propylene glycol dipelargonate, glycerol trioctanoate and mixtures thereof.

The lipophilic material may also be a lipophilic wax. Preferably, less than about 20% by weight of the lipophilic material is one or more lipophilic waxes, particularly where non-greasy and non-sticky compositions are desired. As used herein, the term lipophilic waxes, refers to lipophilic materials that are solid at room temperature, but melt at elevated temperatures. Preferred lipophilic waxes are those selected from the group consisting of insect waxes, such as beeswax, animal waxes, such as lanolin, plant waxes, such as carnauba, mineral waxes, such as ozokerite, petroleum waxes, such as paraffin wax, synthetic waxes, such as polyethylene, and mixtures thereof.

The specific composition and amount of the lipophilic material that is used for a particular composition is a function of the aesthetic and functional properties desired for that composition. The aesthetic and functional properties that may be controlled by a person skilled in the art by varying the composition and amount of lipophilic material used in the composition of the invention include, for example, emolliency, skin feel, and rate of absorbance through the skin.

The compositions of this invention also comprise from about 0.5% by weight to about 28.5% by weight of a cosmetic material chosen from the group consisting of colorants, fragrances, and sunscreens and dermatological agents and mixtures thereof. Colorants useful in the composition of the invention include lipophilic dyes, lakes, pigments and mixtures thereof. Preferred fragrances are the essential oils. Dermatological agents that may be used in our compositions include vitamins, antiinflammatory agents, hydroxyacids, hydroxyacid derivatives, and the like, and mixtures thereof.

Hydroxyacid derivatives that are useful in this invention include cyclic esters of a hydroxycarboxylic acid having the chemical formula:

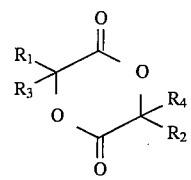

wherein $R_1$ and $R_2$ may be the same or different. $R_1$ and $R_2$ may be selected from the group comprising hydrogen, alkyl, aralkyl or aryl group of saturated or unsaturated, isomeric or non-isomeric, straight chain, branched chain or cyclic form, having 1–25 carbon atoms. Preferably $R_1$ and $R_2$ are selected from the group consisting of hydrogen, methyl, ethyl, propyl, isopropyl, butyl, benzyl, and phenyl. More preferably $R_1$ and $R_2$ are selected for the group consisting of hydrogen and methyl. $R_3$ and $R_4$ may be selected independently from the group comprising hydrogen, a halogen atom and a radical, such as, a lower alkyl, aralkyl, aryl or alkoxy of saturated or unsaturated, isomeric or non-isomeric, straight or branched chain or cyclic form, having 1–9 carbon atoms. Preferably $R_3$ and $R_4$ are hydrogen. The most preferred hydroxyacid derivatives of this invention are lactide (3,6-dimethyl-1,4-dioxane-2,5-dione) and glycolide (1,4-dioxane-2,5-dione).

It is believed that the hydroxyacid derivatives useful in the preferred compositions of the invention break down over time into hydroxyacids upon application to and continued contact with the skin. It is believed that this sustained release of the hydroxyacids over time imparts beneficial effects to the skin.

Sunscreens that may be used include dioxybenzone, 2-ethylhexyl 2-cyano-3,3 diphenylacrylate, 2-ethylhexyl p-methoxycinnamate, 2-ethylhexyl salicylate, homosalate, menthyl anthranilate, oxybenzone, octyl dimethyl PABA, red petrolatum, titanium dioxide, ferulic acid esters, or mixtures thereof. Preferably the sunscreen is titanium dioxide, ferulic acid esters or mixtures thereof. Most preferably the sunscreen is titanium dioxide or ethyl ferulate or mixtures thereof.

The compositions of this invention may also comprise other ingredients that are commonly employed by one of skill in the art in compositions for application to the skin (e.g., stabilizers, antimicrobial agents, antioxidants, and the like).

In the method of the present invention, DBMSA, a lipophilic material and a cosmetic material are combined at a temperature and a period of time sufficient to dissolve substantially all of the DBMSA in the lipophilic material to obtain a solution of DBMSA in the liquid material. The solution is then solidified by cooling it.

The DBMSA, lipophilic materials and cosmetic materials may be combined and mixed together using any means familiar to those skilled in the art. For example, a LIGHTNIN™ Stirrer or a Silverson homogenizer may be used for this purpose.

The heating step is carefully monitored (e.g., by visual means) to ensure that the solution is substantially free of undissolved DBMSA.

In a preferred embodiment of this invention, the DBMSA and the lipophilic material are combined and heated at a temperature sufficient to dissolve substantially all the DBMSA before one or more cosmetic materials are added to the mixture. Preferably, the temperature is about 75° C. to about 200° C. Most preferably the temperature is about 150° C. to about 200° C. Once substantially all the DBMSA is in solution, the cosmetic material is admixed with the mixture and the resulting admixture is cooled to room temperature. Particularly when the cosmetic material is colored or particulate, proceeding in this manner facilitates the ability of the person(s) making the composition to determine that substantially all the DBMSA is dissolved in the lipophilic material.

Preferably, the heated mixture is transferred while still above ambient temperature to the container in which it will be stored, where it is solidified. For example, the heated, still liquid material may be transferred to a lipstick mold, a makeup pan, or a wide-mouthed jar and cooled to about ambient temperature to solidify the mixture.

The compositions of the present invention may be formulated for a wide range of cosmetic applications. For example, the compositions may be formulated as lip area treatment preparations, eye area treatment preparations, sunscreen preparations, antiinflammatory preparations, antiacne preparations, antibacterial preparations, color cosmetic preparations, fragrance preparations, moisturizing preparations, exfoliating preparations, and the like.

The following non-limiting examples illustrate various compositions of the present invention.

EXAMPLES

Example 1

Transparent Lipstick

|  | Component | Parts By Weight |
|---|---|---|
| Phase 1: | Finsolv TN[1] | 48.25 |
|  | Trivent OC-G[2] | 48.25 |
|  | DBMSA | 3.00 |
| Phase 2: | D & C Red No. 21 6921/362[3] | 0.50 |

[1]A $C_{12-15}$ alkyl benzoate-containing composition obtained from Finetex, Inc.
[2]A glycerol trioctanoate-containing composition obtained from Trivent Chemical Co.
[3]A D&C Red No. 21-containing composition obtained from Sun Chemical Corp.

Procedure:

Phase 1 was blended at 175° C. using a LIGHTNIN™ Mixer until a clear solution was obtained. Phase 2 was then mixed into this solution. The resultant mixture was poured into a lipstick mold and cooled to room temperature.

The procedure of Example 1 was also used to prepare the compositions of Examples 2–4.

Example 2

A Low-Wax Lipstick

|  | Component | Parts By Weight |
|---|---|---|
| Phase 1: | Emerest 2388[4] | 39.00 |
|  | Castor Oil USP/Crystal O[5] | 34.00 |
|  | Lantrol (Plain)[6] | 5.00 |
|  | Beeswax - White S.P. 422[7] | 5.00 |
|  | Panalane L-14E[8] | 5.00 |
|  | DBMSA | 4.00 |
| Phase 2: | Flamenco Superpearl[9] | 1.00 |
|  | D&C Red No. 7 Ca Lake 6607/3107[10] | 7.00 |

[4]A propylene glycol dipelargonate-containing composition obtained from Henkel Corp.
[5]A castor oil-containing composition obtained from Caschem, Inc.
[6]A lanolin oil-containing composition obtained from Henkel Corp.
[7]A beeswax-containing composition obtained from Strahl & Pitsch.
[8]A polybutene-containing composition obtained from Amoco Chemicals.
[9]A mica/titanium dioxide-containing composition obtained from Mearl Corp.
[10]A mixture composed of 30 parts by weight D & C Red No. 7 Calcium Lake-containing composition (obtained from Hilton-Davis Chemical Co.), and 70 parts by weight Castor Oil USP/Crystal O. The mixture is combined in a stainless steel mixing container and blended with a Hockmeyer high energy disperser. The mixture is then passed through a three-roller mill twice until a "fineness of grind" reading of greater that 7 on the North scale of a Hegman gauge is obtained.

The composition of Example 2 is useful for providing an aesthetically pleasing, non-sticky, non-greasy transfer of color to the lip area.

Example 3

A Sunscreen Stick

|  | Component | Parts By Weight |
|---|---|---|
| Phase 1: | Finsolv TN | 87.00 |
|  | DBMSA | 3.00 |
| Phase 2: | Ethyl Ferulate[11] | 5.00 |
|  | Tioviel FIN[12] | 5.00 |

[11]An ethyl ferulate-containing composition obtained from ICN Biochemicals, Irvine, Ca.
[12]An ultra fine titanium dioxide-containing composition (40% by weight in an $C_{12-15}$ Alkyl Benzoate) obtained from Tioxide Specialties Ltd.

This composition provided a Sun Protection Factor (SPF) of approximately 16.8, as measured by the in vivo method (See: "Sunscreen Products for Over-The-Counter Human Drugs, Proposed Safety, Effective and Labeling Conditions", Department of Health, Education, and Welfare, Food and Drug Admin., *Federal Register* 43(166), Part II, pp. 38206–38269 (1978)).

Example 4

An Exfoliating Preparation

|  | Component | Parts By Weight |
|---|---|---|
| Phase 1: | Finsolv TN | 44.50 |
|  | Castor Oil USP/Crystal O | 44.50 |
|  | DBMSA | 3.00 |
| Phase 2: | Salicylic Acid USP (Powder)[13] | 2.00 |

-continued

| | Component | Parts By Weight |
|---|---|---|
| | Silicone 200 Fluid - 500 Cts[14] | 5.00 |
| | Vitamin E/Linoleate[15] | 1.00 |

[13] A salicylic acid-containing composition obtained from Rhone-Poulenc Inc.
[14] A dimethicone-containing composition obtained from Dow Corning Corp.
[15] A tocopheryl linoleate-containing composition obtained from Roche Products Ltd.

Example 5

A Facial Makeup

| | Component | Parts By Weight |
|---|---|---|
| Phase 1: | Castor Oil USP/Crystal O | 4.03 |
| | FD&C Yellow No. 5 Al Lake B3014[16] | 0.64 |
| | D&C Red No. 6 Lake C19-022[17] | 0.50 |
| | D&C Red No. 7 Lake C19-011[18] | 0.38 |
| | FD&C Blue No. 1 Al Lake (Lakoline)[19] | 0.01 |
| | Pure Oxy Red 7054/3080[20] | 0.36 |
| | Titanium Dioxide 328 USP[21] | 1.08 |

[16] A FD&C Yellow No. 5 (Aluminum Lake)-containing composition obtained from Warner-Jenkinson Cosmetic Colors.
[17] A D&C Red No. 6 (Barium Lake)-containing composition obtained from Sun Chemical Corp.
[18] A D&C Red No. 7 (Calcium Lake)-containing composition obtained from Sun Chemical Corp.
[19] A FD&C Blue No. 1 (Aluminum Lake)-containing composition, obtained from Warner-Jenkinson Cosmetic Colors.
[20] An iron oxides-containing composition obtained from Warner-Jenkinson Cosmetics Colors.
[21] A titanium dioxide-containing composition obtained from Sun Chemical Corp.

| | Component | Parts By Weight |
|---|---|---|
| Phase 2: | Schercemol DIS[22] | 63.00 |
| | Ceraphyl 791[23] | 11.00 |
| | DBMSA | 4.00 |
| Phase 3: | Mica 280 BC[24] | 10.00 |
| | Speron P-1500[25] | 5.00 |

[22] A diisopropyl sebacate-containing composition obtained from Scher Chemicals, Inc.
[23] An isocetyl stearoyl stearate-containing composition obtained from ISP Van Dyk Inc.
[24] A mica-containing composition obtained from Warner-Jenkinson Cosmetic Colors.
[25] A silica-containing composition obtained from Presperse Inc.

Procedure:

Phase 1 was blended in a three-roller mill until it was homogenous. Phase 2 was heated at 175° C. until a clear solution was obtained. Phases 1 and 3 were then added to the phase 2 solution and the resultant mixture was poured into a makeup pan and cooled to room temperature.

Example 6

A Solid Fragrance Stick

| | Component | Parts by Weight |
|---|---|---|
| Phase 1: | Emerest 2388 | 92.00 |
| | DBMSA | 3.00 |
| | Fragrance | 5.00 |

Phase 1 was blended at 175° C. using a LIGHTNIN™ Mixer until a clear solution was obtained. The solution was poured into a mold and cooled to room temperature.

Example 7

Transparent Skin Treatment Stick

| | Component | Parts by Weight |
|---|---|---|
| Phase 1: | Finsolv TN | 96.00 |
| | DBMSA | 3.00 |
| Phase 2: | Lactide[26] | 1.00 |

[26] A lactide-containing composition obtained from Aldrich Chemical Co.

Procedure

Phase 1 was heated, with stirring, to 180–185° C. or until the DBMSA was dissolved and a clear solution was obtained. Phase 2 was then mixed into this solution. The resultant mixture was poured into a mold and cooled to room temperature.

While the present invention has been set forth in terms of specific embodiments thereof, it will be understood that the invention is defined by the appended claims.

We claim:

1. A solid lipophilic composition suitable for topical application to human skin, which comprises:

(a) from about 1.5% by weight to about 30% by weight of DBMSA;

(b) from about 70% by weight to about 98.0% by weight of a lipophilic material; and (c) from about 0.5% by weight to about 28.5% by weight of a cosmetic material selected from the group consisting of colorants, fragrances, sunscreens, dermatologic agents, and mixtures thereof.

2. The composition according to claim 1 wherein the lipophilic material comprises at least 80% by weight of one or more lipophilic oils.

3. The composition according to claim 2 wherein the lipophilic material comprises at least 95% by weight of one or more lipophilic oils.

4. The composition according to claim 3 wherein the lipophilic oil is selected from the group consisting of castor oil, mineral oil, squalene, fatty acids, fatty alcohols, $C_{12-15}$ alkyl benzoate, propylene glycol dipelargonate, glycerol trioctanoate and mixtures thereof.

5. The composition according to claim 4 wherein the lipophilic oil is $C_{12-15}$ alkyl benzoate.

6. The composition according to claim 4 wherein the lipophilic oil is propylene glycol dipelargonate.

7. The composition according to claim 4 wherein the lipophilic oil is glycerol trioctanoate.

8. The composition according to claim 1 wherein the lipophilic material comprises a lipophilic wax selected from the group consisting of animal waxes, insect waxes, plant waxes, mineral waxes, petroleum waxes, synthetic waxes and mixtures thereof.

9. The composition according to claim 1 wherein the cosmetic material is a colorant selected from the group consisting of lipophilic dyes, lakes, pigments and mixtures thereof.

10. The composition according to claim 1, wherein the cosmetic material is a dermatologic agent selected from the group consisting of vitamins, antiinflammatory agents, hydroxyacids, hydroxyacid derivatives and mixtures thereof.

11. The composition according to claim 10, wherein the dermatologic agent is a hydroxyacid.

12. The composition according to claim 10, wherein the dermatologic agent is a hydroxyacid derivative.

13. The composition according to claim 12, wherein the hydroxyacid derivative has the formula:

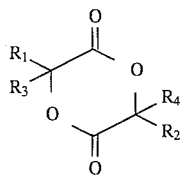

wherein $R_1$ and $R_2$ are independently selected from the group consisting of hydrogen, and a $C_1$–$C_{25}$ alkyl, aralkyl or aryl group of saturated or unsaturated, isomeric or non-isomeric, straight chain, branched chain or cyclic form and $R_3$ and $R_4$ are selected independently from the group consisting of hydrogen, a halogen and a lower alkyl, aralkyl, aryl or alkoxy of saturated or unsaturated, isomeric or non-isomeric, straight or branched chain or cyclic form, having 1–9 carbon atoms.

14. The composition according to claim 13 wherein $R_3$ and $R_4$ are hydrogen.

15. The composition according to claim 13 wherein the hydroxyacid derivative is selected from the group consisting of lactide, glycolide and mixtures thereof.

16. The composition according to claim 15, wherein the hydroxyacid derivative is lactide.

17. The composition according to claim 15, wherein the hydroxyacid derivative is glycolide.

18. The composition according to claim 1, wherein the cosmetic material comprises a sunscreen selected from the group consisting of dioxybenzone, 2-ethylhexyl 2-cyano-3,3-diphenylacrylate, 2-ethylhexyl p-methoxycinnamate, 2-ethylhexyl salicylate, homosalate, menthyl anthranilate, oxybenzone, octyl dimethyl PABA, red petrolatum, titanium dioxide, ferulic acid esters and mixtures thereof.

19. The composition according to claim 18, wherein the sunscreen comprises ethyl ferulate.

20. The composition according to claim 18, wherein the sunscreen is titanium dioxide.

21. A method for applying a cosmetic composition to the skin comprising the step of applying to the skin the composition of any one of claims 1 to 20, or 25.

* * * * *

UNITED STATES PATENT AND TRADEMARK OFFICE
CERTIFICATE OF CORRECTION

PATENT NO. : 5,610,199
DATED : March 11, 1997
INVENTOR(S) : Isaac D. Cohen et al.

It is certified that error appears in the above-identified patent and that said Letters Patent is hereby corrected as shown below:

Column 10, line 23, delete ", or 25".

Signed and Sealed this

First Day of August, 2000

Attest:

Q. TODD DICKINSON

Attesting Officer        Director of Patents and Trademarks